United States Patent [19]

DeBruin-Ashton

[11] Patent Number: 6,014,629
[45] Date of Patent: Jan. 11, 2000

[54] PERSONALIZED HEALTH CARE PROVIDER DIRECTORY

[75] Inventor: Deborah J. DeBruin-Ashton, Tonawanda, N.Y.

[73] Assignee: Moore U.S.A. Inc., Grand Island, N.Y.

[21] Appl. No.: 09/005,687

[22] Filed: Jan. 13, 1998

[51] Int. Cl.[7] ................................................... G06F 17/60
[52] U.S. Cl. ............................ 705/2; 705/14; 707/908
[58] Field of Search .................................. 705/2, 3, 4, 14; 707/908, 910

[56] References Cited

U.S. PATENT DOCUMENTS

| | | | |
|---|---|---|---|
| 3,970,332 | 7/1979 | Alford, Jr. ................................. | 281/31 |
| 4,022,455 | 5/1977 | Newsome et al. . | |
| 4,870,576 | 9/1989 | Tornetta . | |
| 5,029,902 | 7/1991 | Komori . | |
| 5,053,955 | 10/1991 | Peach et al. . | |
| 5,225,976 | 7/1993 | Tawil . | |
| 5,493,490 | 2/1996 | Johnson . | |
| 5,502,636 | 3/1996 | Clarke . | |
| 5,519,607 | 5/1996 | Tawil . | |
| 5,537,314 | 7/1996 | Kanter . | |
| 5,584,025 | 12/1996 | Keithley et al. . | |
| 5,740,425 | 4/1998 | Povilus .................................... | 395/611 |
| 5,778,345 | 7/1998 | McCartney ................................. | 705/3 |
| 5,850,433 | 12/1998 | Rondeau ................................. | 379/201 |

OTHER PUBLICATIONS

Moore, Jr., J. D. "Care may be closer than you think: GeoAccess helps employees find care that's closer to home." The Kansas City Star, Business Section, p. D7, Feb. 1995.

Schwartz, Susana. "Wausau embraces mapping technology." Insurance & Technology, vol. 20, No. 8, ogs. 18–20, Aug. 1995.

Scott, Miriam Basch. "United Airline's personalized directories promote preferred providers." Employee Benefit Plan Review, vol. 52, No. 2, pp. 28–30, Aug. 1997.

"Web–based Maps On Us used to find health care." Newsbytes News Networks (0983–1592), Nov. 1997.

GeoAccess "DirectoryExpert." www.geoaccess.com/communications/directoryexpert.htm (retrieved on Apr. 27, 1999).

GeoAccess "GeoNetworks." www.geoaccess.com/accessanalysis/geonetworks.htm (retrieved on Apr. 27, 1999).

*Primary Examiner*—Allen R. MacDonald
*Assistant Examiner*—Michele Stackey Crecca
*Attorney, Agent, or Firm*—Nixon & Vanderhye P.C.

[57] ABSTRACT

A directory of group physicians for a health care provider service is disclosed in which the directory is tailored to a particular customer of the provider service. Relational databases of physician information, customer information, geographic mapping information, and images and/or advertising information are used to select those physicians, health care providers and health care businesses that are local to a specific customer and are to be printed in a directory for that customer. The selection of physicians from the database may include physicians having specialties that had been used by the customer, or physicians having specialties that correspond to the health care needs of a customer, e.g., customers having young children tend to use pediatricians. In addition, a mapping software program generates a local map for the customer that plots the addresses of the physician to be listed in the directory. The information extracted from databases regarding the customer, physicians, local map and other information is merged with a template directory to print a directory tailored to a particular customer.

15 Claims, 6 Drawing Sheets

PERSONALIZED HEALTH CARE PROVIDER DIRECTORY

FIELD OF THE INVENTION

The present invention relates to the fields of printing of directories and, in particular, to health care directories.

BACKGROUND AND SUMMARY OF THE INVENTION

Group health care service providers publish directories of the physicians and other health care providers (collectively referred to as group physicians) that are members of the group. Customers that have subscribed to the group health care service providers may go to group physicians, and have the service provider pay the physician. The customers pay a fee to belong to the group health care service. The customer does not directly pay the physician, or may pay only a portion of the physician's fee. Customers need to be informed about the group physicians authorized by their group health care service.

The customers of group health care service providers generally obtain their health care from group physicians to obtain the benefits of the group health care service. Group physicians have agreed with the group health care service to, for example, charge reduced fees to customers of the group health care service, bill the group health care service directly (rather than the customer), and may provide other benefits to the customers. The customers must use approved group physicians to receive the benefits (or at least full benefits) of the plan. If the customers go to physicians who are not approved by the health care plan, then the customer may have to pay all (or a relatively-large portion) of the non-group physician's bill. These non-group physicians will not, for example, charge reduced fees or bill directly the group health care service. Accordingly, customers of group health care services desire to use group physicians, and the group health care service providers are motivated to serve their customers by directing them to group physicians.

Directing customers to group physicians has become increasingly more difficult for health care service providers. These difficulties are due, at least in part, to the large number of available group physicians; changes in the names, addresses, specialties, etc. of the group physicians, and the logistical problems associated with distributing current listings of group physicians to all customers of a group health care service provider.

Group health care service providers publish printed directories which list the group physicians authorized under the provider's health care plan. These published directories often provide lists of physicians organized by physician name, by geographic location of the physician's office, and by physician's medical specialty. A directory of group physicians may be voluminous because it includes listings by name, geographic, and specialty listings of all of the group physicians. As the number of group physicians grows in a particular health care plan, the size of the health care directory rows disproportionately because each physician may be listed three or more times in the directory such as in a name list, geographic list, and a specialty list. Accordingly, the name, address, telephone number of each physician in a health care service plan may be repeated three times in the directory of group physicians. With large health care service providers, it is common for their group physician directory to be hundreds of pages, with hundreds of physicians listed on the front and back of every page. Because directories have become voluminous, indices of physicians have also been added to the directories to make them easier to use. The indices add even more pages to the directories. Accordingly, it is common for health care service providers to publish voluminous health care provider directories that repeatedly list all of the group physicians who are a member of the group health care service plan.

Large group physician directories have become cumbersome to use, expensive to print and logistically difficult to distribute frequently enough to be current. Customers of health care service providers often are frustrated when they leaf through the hundreds of pages of a directory to find one physician located near where they live or work, and having a desired specialty. These directories may include tens or hundreds of physicians in a geographic location corresponding to a customer. Even when a customer reviews a geographic section listing for the region near the customer of the directory, the customer may find many more nearby physicians listed than the customer can reasonably investigate and select. The customer often randomly selects a nearby physician from the geographic list of nearby physicians. Presenting the customer with a lengthy list of nearby physicians often does not benefit the customer and serves no useful purpose. Moreover, an excessive number of physicians may also be published in the listing of physicians by specialty. For example, with larger specialties, such as pediatrics and general practice, a single directory may list dozens or more physicians in a given specialty. Moreover, directories tend not to arrange the listings of physician specialties by local geographic areas. Accordingly, a customer searching for physicians by specialty must scan through the entire list of physicians with that specialty to find a physician geographically nearby the customer. In short, health care plan customers have become increasingly frustrated with the large directories of group physicians that are cumbersome and unwieldy.

Voluminous directories of group physicians are also expensive to publish, print and distribute. Each health care provider service must periodically distribute directories of group physicians to each customer. As new customers join the plan, new directories must be printed and distributed to the new customers.

Group physician directories must be updated regularly to reflect the new physicians joining the health care service, and the physicians that left the service. Customers become frustrated if, upon calling a physician listed in a directory, the customer learns that the physician is no longer associated with the health care service or is not accepting new patients. If the physician is not associated with the health care service, the customer may nevertheless go to that physician and forfeit the benefits of the health care service plan. In addition, new physicians joining the health care plan will not receive many new patients coming to them from the health care service plan unless the new physician's name is published in the group physician directory. Physicians not listed in a directory cannot be found in the directory, and customers will not know that those doctors have joined their health care service plan. Accordingly, group physician directories must be routinely updated to show the current list of physicians active in the health care plan.

Updating health care directories is expensive and time consuming. The health care service provider generally maintains computerized lists of all current group physicians. These computerized lists are regularly updated as physicians change their affiliation with the health care service plan, change specialties and change office addresses.

Group health care service providers must periodically print and distribute the updated directories to the customers.

Large directories with many pages are more expensive to print and distribute than would be thin directories with few pages. In addition, the cost and logistical problems associated with distributing voluminous group physician directories tends to cause health care service providers to infrequently, e.g., annually or quarterly, publish updated directories. Even the most-current directories of a health care provider may be as much as one year out of date. Accordingly, customers looking through current directories may identify physicians who are no longer associated with the health care service plan, who are no longer accepting patients, or physicians who have moved away from the offices listed in the directory. Accordingly, large health care directories for group health care services are cumbersome, expensive and often out of date.

Directories are too large to be placed in an easily-accessible location for the customers, such as near the customer's telephone. Instead, directories tend to be stored in the bottom of drawers in a home or office, or other place where they are easily forgotten. Accordingly, the large size of directories results in most directories not being stored such that it can be readily used by customers of a health care service provider.

In the past, efforts to remedy the problems associated with large health care directories have been minimally effective. For example, to reduce the cost and size of directories, health care service providers have used small print type and inexpensive paper on which to print their directories of group physicians. Such directories look and feel more like a small telephone directory, rather than a high-quality commercially-printed document. While small type and low-cost paper reduces the cost and size of the directory, the small type makes the directory harder to read. The cheap paper is often an off-gray color that is easily torn and damaged. To reduce the size of directories, health care service providers often print minimal information about group physicians, such as their name, address, telephone number and specialty. Not printed in the directories is other information, such as whether a physician is currently accepting new patients, has weekend or extended office hours, is certified by recognized medical boards, is admitted to certain hospitals and is specially trained in certain sub-specialties. Accordingly, prior attempts have not been particularly successful in improving directories of group physicians for health care service providers.

SUMMARY OF INVENTION

There is a long-felt need for an improved directory of group physicians for health care service providers. The present invention fulfills this need by combining the technologies of computer relational databases, advanced variable print processes, color glossy printing technology and knowledge gained from marketing services to individual customers. The invention utilizes relational databases of physician information, customer information, geographic mapping information, and regarding images and/or advertising information. Data is intelligently extracted from each of these databases, such as by sorting the physician database by physician type, e.g., specialty, and zip code, to identify physicians having offices in the zip code of a customer and having specialties corresponding to a particular customer's needs.

The data extracted regarding physicians within the zip code of the customer and having specialties corresponding to the customer may be further limited by selecting only a predetermined number, e.g., a dozen, of physicians (on a semi-random basis or applying some other criteria, such as only physicians accepting new patients), to narrow the number of physicians selected from the database to a relatively-small number of physicians for presentation to the public. The selection of physicians from the database may include physicians having specialties that had been used by the customer or physicians having specialties that correspond to the health care needs of a customer, e.g., customers having young children tend to use pediatricians. Accordingly, the small number of physicians selected for presentation to a customer include those physicians previously selected by the customer, and a listing of other physicians having specialties corresponding to the customer's needs and having office addresses geographically nearby the customer.

The invention further incorporates a local geographical map created for the customer from a mapping database and mapping software application. The map may be a street map that has at the center of the map the customer's home address (or office address) so as to generate a local street map of the area surrounding the customer. The mapping software application program may further plot on the street map the customer's home address and the addresses of the physicians to be listed in the directory. In addition, offices of other health care providers and businesses, such as pharmacies, may be plotted on the street map. The map with the plotted addresses and the list of selected physicians are printed in a short group physician directory that is tailored to the one specific customer to whom the directory is addressed.

In addition, the invention may access databases of images and advertising materials which are to be printed in conjunction with the selection of physicians and mapping information. The images may include high quality, glossy color pictures of the health care service provider's logo, office building or other picture symbolizing the health care service provider. The image may be of some other business, e.g., a pharmacy, which is to be printed as advertisement on the directory. In addition, coupons and other advertising materials for health care service providers or health care related businesses may be selected that correspond to the individual customer. For example, a customer's database may have information indicating the customer has infant children and, thus, coupons for discounts on diapers from the local drug store may be selected from the image and advertising database and included in the printing of a directory for that customer with infants.

A computer system accesses each of the databases and extracts the information needed for printing on a single sheet (or a few sheets) a high quality, e.g. print and images, printed document that lists a relatively-small number of physicians nearby the customer, a map showing the offices of these physicians, and having specialties corresponding to the customer. The high quality print document may include a high definition color photograph of the health care service provider or some other advertising image. A street map may be printed that includes plotting symbols identifying the addresses and location of the customer's home and of the addressee physician whose name and specialty are listed on the document. Furthermore, the printed document may include coupons or other advertising materials which can be used to obtain discount health care service or health care products by the customer.

All of the information printed on the document is specifically selected to correspond to the particular customer to which the printed directory is addressed. The map printed on the document is specifically created for that customer.

Similarly, coupons and other advertising materials are selected that correspond to the perceived needs of the customer. Accordingly, the printed, short group physicians health directory is created for a particular customer, and has only information that directly relates to that customer.

The invention is more advantageous over the prior art because the invention does away with the cumbersome and costly health care directories that had too many pages and presented too many group physicians. A health care directory printed in accordance with the invention is specifically tailored to a particular customer, and does away with information regarding physicians that the customer will not likely ever use. In contrast, prior directories of group physicians listed every physician, even though each customer would likely not use the vast majority of the listed physicians. With the present invention only physicians local to a customer are printed on the document presented to the customer. Moreover, physicians having specialties that the customer is not likely to use are not presented to the customer by the directory. In addition, the number of documents local to the customer and having specialties corresponding to the customer may be limited to a relatively-small number, e.g., 6 to 12, such that the customer is not presented with an excessive number of physicians.

Another advantage of the invention is that it is much less costly to distribute a group physician directory that is one sheet than it is to print and distribute the large page-numbered directories. For example, the current invention can be generated on a single sheet, printed double-sided and folded to form a four page document that is mailed to customers. This document can, on one side, list the names of half a dozen to a dozen physicians and their specialties in which the customer may be interested. The opposite side of the postcard may show a map that identifies the customer's address and shows the addresses of the identified physicians. This one sheet directory may be small enough for a customer to place underneath a telephone for quick access, or to mount onto a refrigerator so as to be easily visible when needed. Moreover, the cost of creating, printing and mailing the directory can be at least partially recovered by advertising fees generated from the health care business that pay to have coupons and other advertisements printed in the directories.

The invention may also include the advantage of listing physicians that the customer has previously used, as well as presenting new physicians that the customer may not have previously used. For example, a new physician just joining a health care service plan may be listed on a relatively-high portion of the directories compared to long-standing physicians. Alternatively, the selection of physicians that are local to a particular customer may be randomly selected such that the names of all the physicians in the health care service are printed on customer health care directories at relatively the same rate for other physicians. Accordingly, the exposure provided to physicians in the directories can be controlled in the printing of directories.

The invention may be implemented as a method for printing a group physician directory using a computer system having access to relational databases for customers of a health care provider service, for group physicians that are members of the health care provider service, and for mapping data, and to a printer, where the method comprises the following steps:

a. designing a directory template having fields for a customer name, customer address, a listing of group physician names and addresses, and a map;

b. selecting a customer name from a listing of customers for which personalized health care provider directories are to be printed;

c. for a customer selected in step (b), obtaining from the customer database information regarding an address for the customer;

d. determining a geographic region corresponding to the address of the customer;

e. accessing the database for group physicians, and selecting group physicians having office addresses within the geographic region determined in step (d);

f. generating a map of the geographic region determined in step (d) and plotting on the map the addresses of the customer and the physicians selected in step (e);

g. importing information into the respective fields of the template of the health care provider directory, the information including the customer name selected in step (b), the customer address obtained in step (c), the group physicians identified in step (e), and the map generated in step (f);

h. printing the directory by printing the template of the health care directory with the information imported into the template in step (g).

These and other advantages of the invention will become apparent in the attached drawings and detailed description of the invention.

BRIEF DESCRIPTION OF THE DRAWINGS

FIGS. 2(*a*) through 2(*c*) is a high-level flow chart showing an exemplary computerized software application for implementing the current invention.

FIGS. 3(*a*) and 3(*b*) are drawings of front and back sides of an exemplary health care directory printed in accordance with the present invention.

DETAILED DESCRIPTION OF THE DRAWINGS

Figure 1:
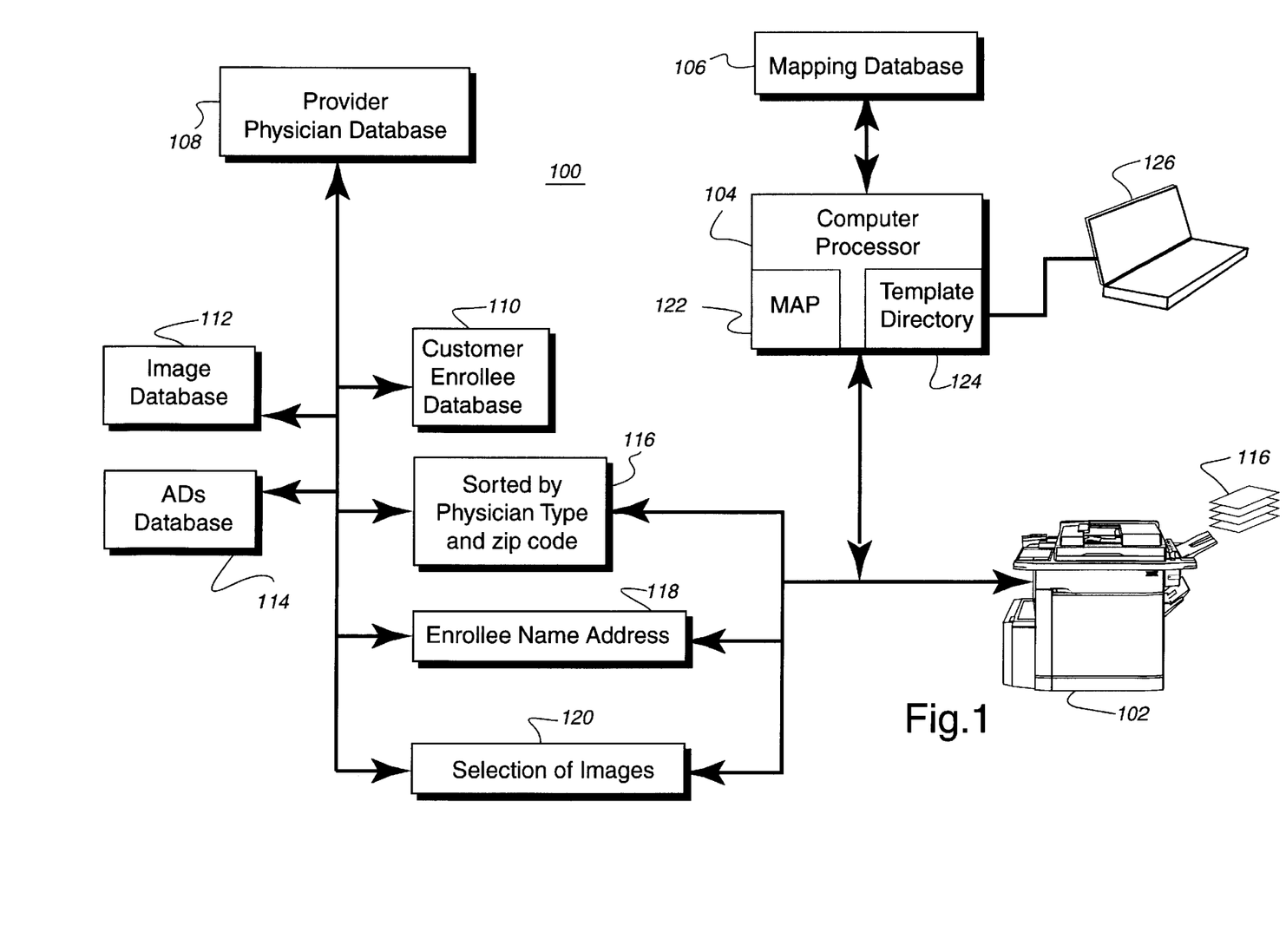
FIG. 1 shows a computer system having access to multiple databases and a variable print system.

FIG. 1 is a schematic diagram of a computer system 100 and a variable print station 102 which together shows an exemplary embodiment of the present invention. The computer system 100 includes a computer processor 104 (such as an IBM Compatible Personal Computer) that can access several databases, including a provider physician (group physician) database 108, customer (enrollee) database 110, an image database 112 and an advertisement and/or coupon database 114. The computer processor has at least read access to each of these databases and may have write access to one or more of the databases. In addition, the computer processor interacts with a variable print engine 102 (or other printer system) which prints group physician directory documents 116 by merging data processed by the computer processor 104 with data extracted from one or more of the databases accessible to the computer processor and/or the variable print engine.

The group physician database 108 may include data fields for physician name, physician office address, physician specialty, and optionally fields for other data such as whether the physician is accepting new patients, medical certifications held by the physician, and other information which may be of interest to customer enrollees of the health service plan. The group physician database includes information on physicians and other health care providers who are associated with the health care service provider that is publishing the directory. The group physician database 108 is searchable at least by physician name, office address and/or specialty.

The customer-enrollee database 110 has data fields for the names of customers enrolled in the group health care service plan. Additional database fields are provided for the customer's address, and may optionally include fields for the names of physicians previously used by the customer, the types of medical specialties the customer has used in the past or identified as specialties the customer may use. The database may include further fields having other information such as whether the customer is male or female, the customer's age, the ages of the customer's children, and other information which might be relevant to selecting group physicians, specialties or health care services for the customer. The customer database 110 is searchable on the basis of customer name and, optionally, on the other fields in the database.

A mapping database 106 is accessible to provide street map information to the computer processor 104. The mapping database may include a complete street and regional map (maps) for the entire region covered by the health care service provider operating the computer system 100. If the computer system 100 is used to generate directories for more than one health care service provider, then the mapping database may have street map data for regions corresponding to all health care service providers for which directories may be printed. The mapping database is used by the computer processor 104 to generate street maps of the immediate geographical area surrounding a selected customer's residence or office. The mapping database may also be used to define a geographic region corresponding to a selected customer. Suitable commercially-available exemplary software applications exist for generating street maps based on a customer address, and for determining a geographic region surrounding the customer's address.

Other databases that may be used in connection with the computer system 100 include an image database 112 that includes images that may be included in the directory being printed by the variable print engine 102. The image database may include data fields for printable images and associated fields that may, for example, identify the format of the image, an image title, and a health care service provider associated with the image. An advertisement database 114 may have information regarding advertisements and/or coupons that are selectable by the computer processor 104 for inclusion with directories 116. The advertisement and coupon database 114 may be searchable on the basis of the health care businesses (such as pharmacies, medical laboratories, recreational and exercise clubs, and/or other health associations) that have paid the health care provider service to have their advertisements and/or coupons included with the directories published by the health care service provider.

In a typical print process performed by the computer system 100, a customer's name and address would be obtained from the customer database 110, and, if available, the customer's preferences for physicians and physician specialties. The address corresponding to the customer is used by the computer processor 104 and mapping database 106 to determine a geographic region local to the customer. For example, the geographic region may be an area that is within one-half mile of the customer. Alternatively, the area corresponding to the zip code of the customer may be specified as the local geographical region for the customer.

Once the localized geographic area corresponding to the customer has been determined (either by zip code or through other means using the mapping database 106), the group physician database 108 is searched to identify those group physicians and other group health care providers having offices located within the specified local geographic area for the customer. The selection of group physicians and health care providers within the specified geographic area may be further limited by selecting only those physicians having a particular specialty (physician type). The selected group physicians and health care providers are temporarily stored in a physician memory location 116 associated with the computer processor 104 and/or variable printer 102. The selected physician memory location may have separately accessible locations for the physicians' names, specialties, addresses and telephone numbers. In addition, the physician memory location may have separately accessible and searchable memory locations for each of the physicians selected for printing in the directory.

For example, if the customer database 110 has fields that identify the physicians that have treated the customer, and the physician database has fields that identify the specialties of those physicians who previously treated the customer, then the computer processor may select those physicians who previously treated the customer and other physicians who have the same specialties of the treating physicians and are local to the customer. Moreover, other information stored in the customer database regarding the customer may be used to, for example, select pediatricians when the customer database indicates that the selected customer has a child under 13 years of age. As another example, if a customer has previously used physician John Smith, who is a cardiac specialist, the group physicians and health care providers selected for that customer will include John Smith, a selection of cardiac physicians in the geographic region for the customer, a selection of general internists (which is a common physician specialty used by many customers), and a selection of dieticians (because a listing of dieticians are provided to all customers who have been treated by a cardiac specialist).

If the number of selected physicians that are both within the geographic region of the customer and have specialties corresponding to the customer exceeds a threshold number of physicians, e.g., twenty-four, then a random selection process may be employed by the computer processor to reduce the number of selected physicians to the threshold number of physicians. For example, if the threshold for the number of physicians to be listed in a directory is two dozen, but fifteen general intern physicians have office addresses within the geographic region of the customer, a cardiac physician has previously treated the customer, six other cardiac physicians are found in the group physician databases as having office addresses within the geographic region corresponding to the customer and there are eight dieticians local to the customer, then the computer processor will reduce the total number of physicians to two dozen by, for example, selecting the one previously-used cardiac physician, and randomly selecting five of the other cardiac physicians and six of the dieticians to arrive at a list of two dozen total physicians and health care providers. At the conclusion of the selection process, those remaining physicians and health care providers who have offices within the geographic region of the customer and specialties corresponding to the customer, or are physicians previously selected by the customer, are temporarily stored in a physician data memory location 116 for further processing and printing. The data memory location 116 may be arranged to include a small database for the selected physicians and group health care providers, having data fields for their name, address, telephone number and specialty.

A customer memory location 118 stores the selected customer's name and address in, for example, separately-accessible memory locations. In addition, stored in memory location 120 are selected images from the image database 112 and/or advertisements or coupons from the ads database 114. The selected image may be designated to be printed on each directory 116 in a particular batch of directories. Alternatively, the image may be one of several selectable images that the computer processor 104 selects on some predetermined basis, which basis may be a random selection of a group of images designated by the directory designer. The human designer of the format of the directory 116 can make the designation of the predetermined method for selecting one or more images for printing on the directories.

The coupon and/or advertisements to be printed with the directory 116 may correspond to those health care businesses that have paid advertising fees to the health care service provider publishing the directories. The health care businesses may designate the advertisements and/or coupons stored in the database 114 to be printed on the directories. In addition, the advertisements and/or coupons database may include data fields that designate the types of customers or physicians' specialties the advertisements or coupons are to be used. For example, coupons for discount eyeglasses may be stored in the ads database with a data field that indicates the coupon corresponds to the medical specialty of opticians. Customers for whom the database 110 indicates the customer wears glasses, may receive a coupon for the discount eyeglasses printed in the directory printed for them. The coupons and/or advertisements may be stored in memory with the images for the directory.

The local map stored in memory location 122 is, for example, a street map of the geographic area surrounding the selected customer whose name is stored in the customer name memory location 118. The map is generated from data stored in the mapping database 106 and by a mapping software application executed by the computer processor. In addition, the map includes indicia, e.g., map symbols, showing the addresses of the customer and group physicians whose names will be listed on the directory 116. The mapping symbols may vary by physician, physician specialty, and health care business. For example, an icon of eyeglasses may be plotted on the map for the address of an optometrist. Other easily-identifiable icons may be used to identify the customer's general internist physician, pediatrician or a health business, such as a pharmacy. The map is stored in memory 122 in conjunction with the other memory locations of the customer's name, 118, listing of physicians 116, and selection of images and/or coupon/advertisements 120.

The memory locations in the computer system are used to temporarily store a particular customer's name and address 118, the selected physicians' name, address and specialties 116, a local map 122 for the customer and a selection of images and/or addresses/coupons 120. The information is stored briefly in memory until read by the computer processor 104 and/or variable print engine 102 to print the group physician directory 116 for the customer. After the information is obtained from the memory locations 116, 118, 120 and 122, and is used to print a directory, the memory locations are rewritten with information for the next customer for whom a directory is to be printed. Thus, the data needed to print the directories are brought together from the physician database, customer database and mapping database, and temporarily stored in memory until the computer processor and variable print engine are ready to merge the information with a map 122 and template of a group physician directory 124.

A template of the health care directory is stored in a memory 124 associated with a computer processor. The memory location 124 may be integral with the computer processor, just as is the map memory location 122 may be integral with the computer processor. The template directory may be a template electronic document of a group physician directory. The template may include fixed images and/or fixed text to be printed on each directory. In addition, the template directory may have fields blocked out for variable print information, such as the customer's name and address from memory location 118, the listing of physicians, from memory location 116, a map from memory location 122, and a discount coupon from memory location 120. The template directory may be created on a computer workstation 126 by a marketing or artistic personnel associated with the health care service provider.

The computer processor determines when all of the information necessary to generate a health care directory for a particular customer is ready for printing. At that time, the processor issues a print command that causes the template directory 124 to be downloaded to the variable print engine. The template directory may include commands in its variable fields (and fixed image or text fields) that identify the memory locations from which to extract the information to be inserted and printed in those fields by the variable print engine 102. For example, the template directory may have a blocked out map field area that identifies the area of the directory into which the map is to be inserted and includes a command identifying the map memory location 122 from which the map information is to be read. Similarly, the customer's name and address, listing of physicians and selection of images and/or coupons can be accessed by a command on corresponding fields of the template directory so that the memory locations identified in the template directory are accessed to obtain the information to be printed in those fields.

Figure 2A:
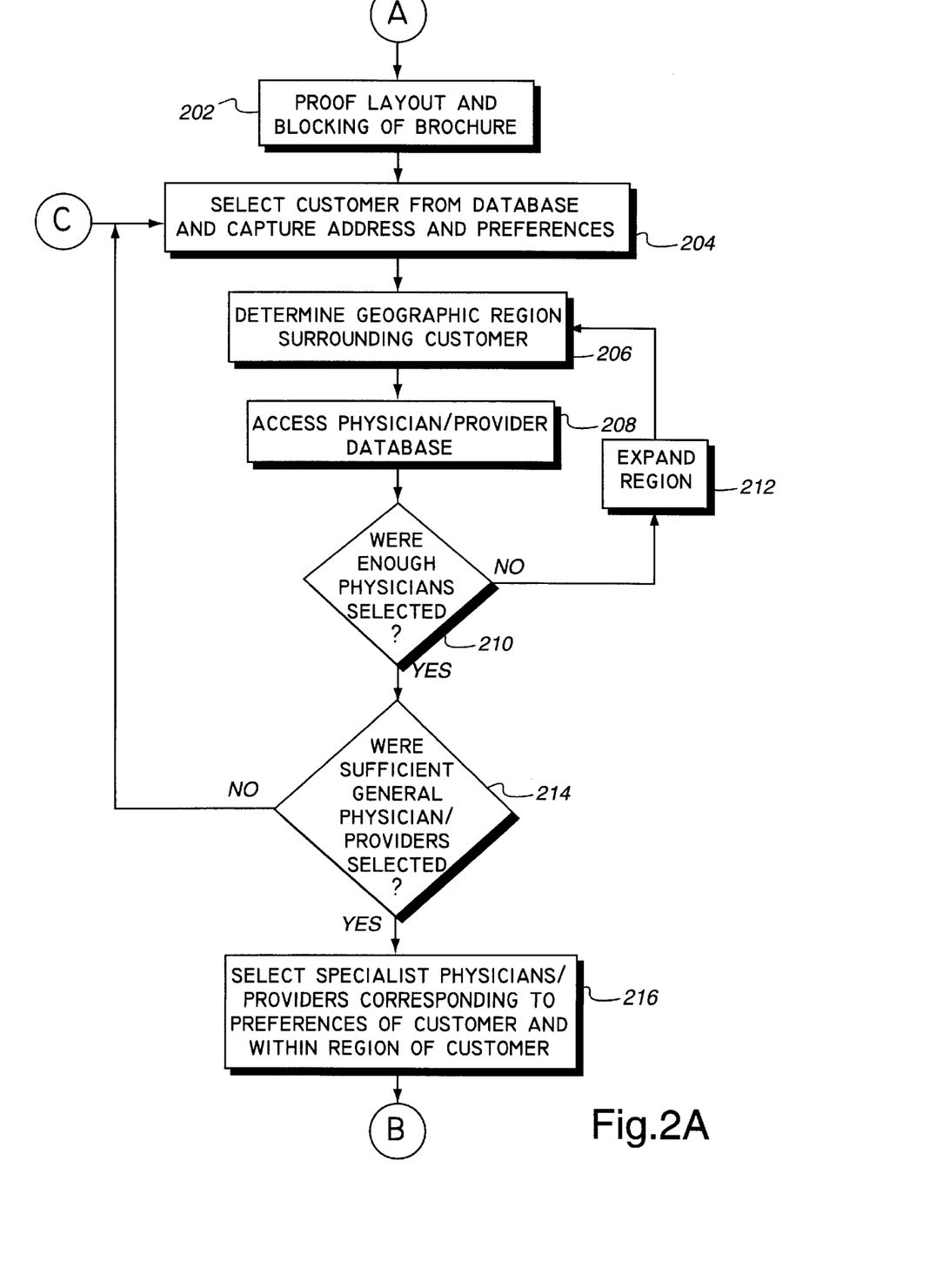
Figure 2B:
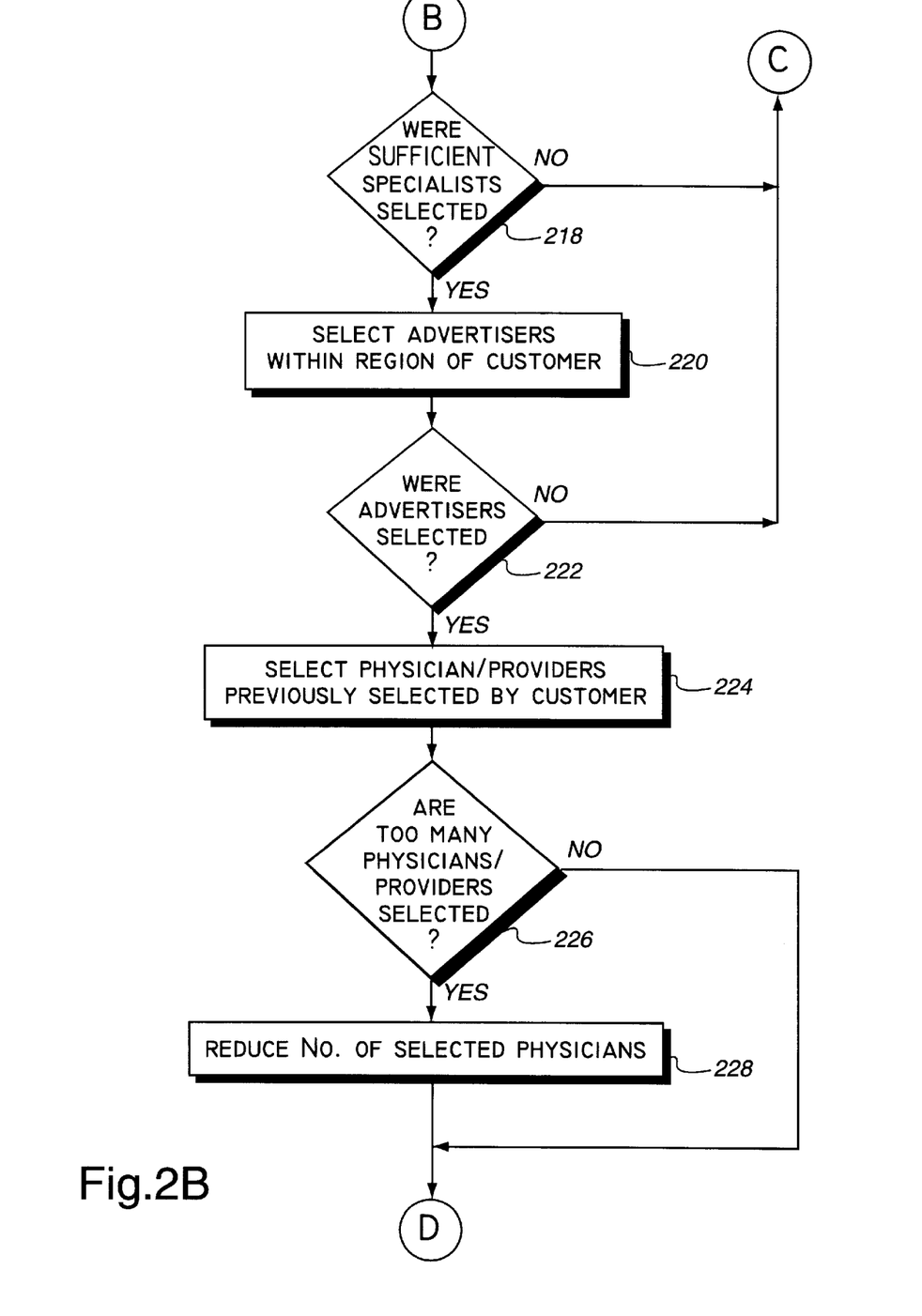
Figure 2C:
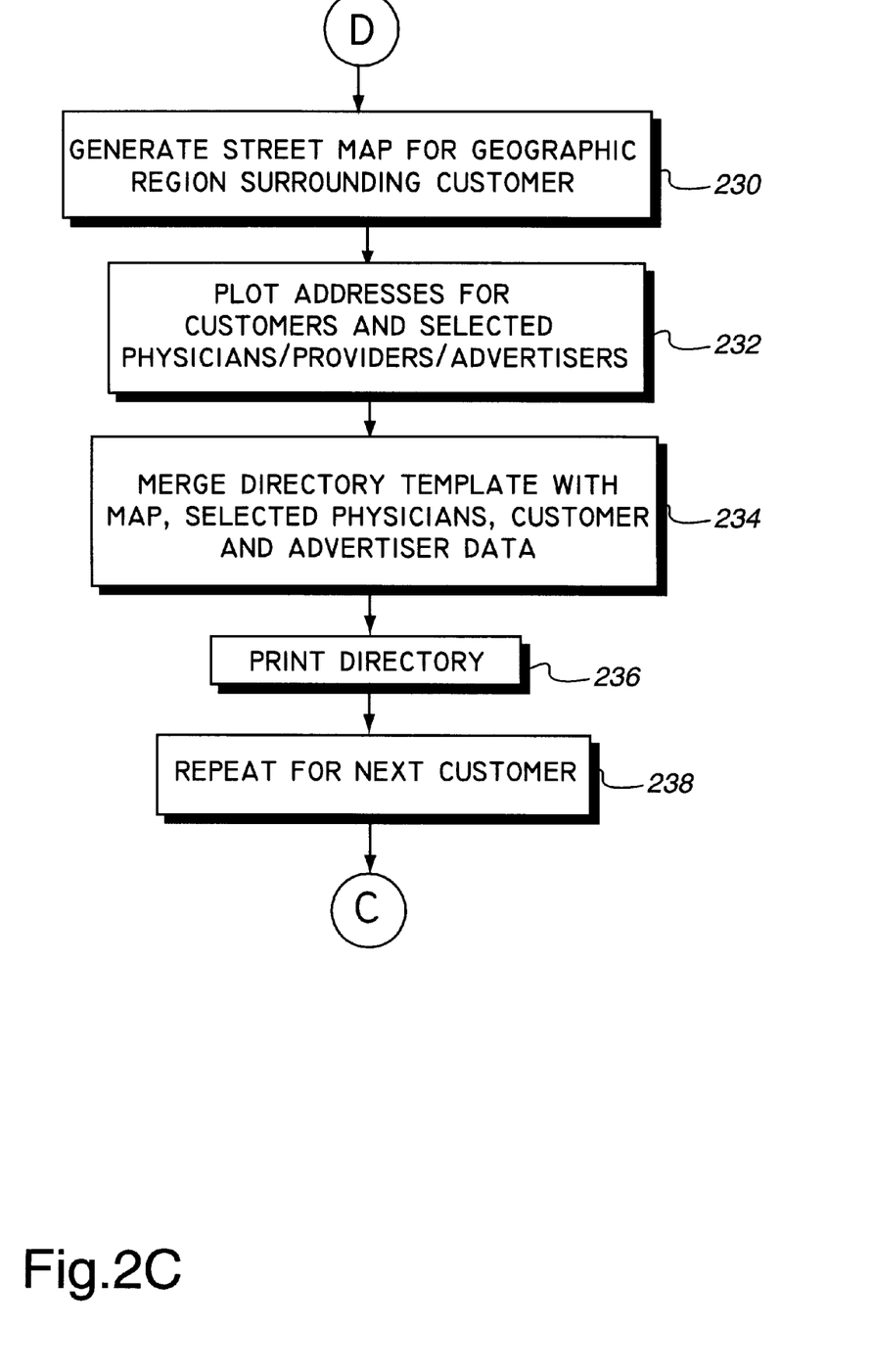

FIGS. 2A, 2B and 2C are flow charts of an exemplary process for creating and printing a personalized group physician health care directory. In step 202, a marketing professional, artist or other individual creates a template for a group physician directory using a computer workstation 126. The individual designing the directory template creates a layout for the template that specifies the format for the directory, such as whether the directory is a single sheet folded to form a four-page brochure having printing on four pages. In addition, the designer of the directory creates a layout that specifies the location on the directory of both fixed and variable print information. For example, the individual creating the template may enter in through the computer workstation 126 the fixed text to be printed on each brochure and access via the image database 112 any of the images to be included as fixed images on each and every directory.

The variable print information to be printed on the directory template is blocked out by the designer to specify the locations in the directory where the variable information (text and images) is to be placed during printing. In addition, an area in the directory template is defined for listing physicians. A physician's field is defined in the template so that the physicians' names, addresses and telephone numbers will be printed in the specific location of the directory as variable information with the printing of each directory. Each field of the directory template may include information defining the number of characters and/or area covered by the field of the template, and a command identifying the memory location(s) in the computer system 100 having the information to be inserted into the field. Once the brochure template is completed, the designer proofreads the template to ensure that it is correct and may have sample directories printed to confirm that the brochure is ready for full printing.

The brochure template may be set up using a computer system 126 such as an Apple Macintosh® having a document design software program, such as Quark XPressX™, and an image processing program, such as the Adobe PhotoShop™ program. The completed template directory is stored in template directory memory 124 of the computer processor. The operator of the computer system invokes a print command to cause the computer processor 104 to begin assembling the information needed to print the directory. The operator may also specify certain parameters regarding the customers for whom the directory is to be published, such as limiting the printing of directories to customers who have joined the service provider in the preceding three months. The computer processor in step 204 selects a subscriber name from the customer database 110. In addition, the customer's address and preferences, e.g., previously-selected physicians and physician specialties, may also be obtained for the selected customer from the customer database.

In step 206, the address information for the selected customer is used by the mapping software application and mapping database 106 to determine a geographic region that is local to and surrounds the customer. The geographic region surrounding the customer may be determined by zip code or by some other algorithm for determining a local geographic region for the customer, such by determining a one-half mile radius around the customer's address.

Once the geographic region for the selected customer is determined, the group physician database 108 is accessed to identify those group physicians and other health care providers having office addresses within the geographic region defined for the customer in step 208. In step 210 a determination is made as to whether the number of physicians and health care providers selected as having addresses within the geographic region surrounding the customer is a sufficient number for printing in the directory. If the number of physicians and providers selected is fewer than a threshold number, such as two dozen, then in step 212 the geographic region corresponding to the customer is expanded to include a broader geographic area so that additional physicians and health care providers may be included in the directory. Once a sufficient number of physicians and health care providers having office addresses within the geographic region surrounding the customer has been selected, then the selected physicians may be sorted by their specialties.

The specialties of the physicians are selected for printing in the directory. The selected specialties may include certain general specialties and other specialties specific to the customer. For example, of the selected physicians having addresses within the customer's geographic region, the general internists (and any other general purpose specialty, e.g., family medicine) may be selected for printing in all directories in step 214. A threshold, e.g., three physicians, may be set for a minimum number of general intern physicians to be listed in the directory. If an insufficient number of general intern physicians are selected, then the geographic region corresponding to the customer may be expanded in steps 212, 206 and 208 in order to increase the number of general internists selected for the customer's directory.

Similarly, the specialists corresponding to the customer are selected from the list of physicians and health care providers having addresses within the geographic region surrounding the customer, in step 216. The types of specialties to be printed in a particular customer's directory may be determined based upon preferences specified for the customer in the customer database 110. For example, if the customer has previously selected specialists in the fields of urology, pediatrics and psychiatry, then physicians with those specialties are selected from the physicians having offices in the geographic region for the customer. In step 216, the process may identify specialties that may be of interest to the customer, such as obstetrics and gynecology for female customers, pediatrics and allergy specialists for customers having children, ophthalmology for customers wearing eyeglasses and gastroenterology for customers who are 60 years or older. Information regarding customers used to select specialties that may be of interest to a customer may be extracted from the customer database and used to identify those specialties that correspond to the customer. If the number of specialist physicians and health care providers that have specialties corresponding to the customer, and that have offices within the geographic region surrounding the customer is less than some threshold level, then in step 218 the process expands the geographic region in step 212 to increase the geographic area used to identify specialists.

In step 220, advertisers who have paid to include their advertisements and/or coupons in directories, and that have office addresses within the customer's geographic region are identified. If an insufficient number of advertisers are identified, then in step 222, the geographic region corresponding to the customer is expanded to locate sufficient advertisers in the geographic region. At the completion of step 222, a selection of at least a sufficient number of physicians (both general internists and specialists), health care providers and advertisers should be obtained for inclusion in a directory. In step 224, those physicians and health care providers that have been previously selected by the customer, as indicated in the customer database 110, are selected for inclusion in the directory in step 224. If too many physicians and/or providers have been selected in step 226, then the number of selected physicians and providers is reduced to some threshold number, e.g., 24, for inclusion in directories.

The determination of whether too many physicians and providers have been selected can be done on an entire group basis for all physicians and providers regardless of specialty to be printed in the directory. In addition, the number of physicians and providers for each specialty to be included in the directory may be evaluated to ensure that the number of listed physicians is not too many. The process of reducing the number of selected physicians to be listed in the directory may include a random selection process for physicians to ensure that all physicians are on average listed in an equal number of directories. Alternatively, other selection algorithms may be used for reducing the number of physicians, such as applying weighing factors to the selection process, such that physicians who have newly joined the health care service plan are represented in a higher proportion of directories, than are physicians and providers that have been with the health care service provider for an extended period of time and are likely have a complete group of clients.

Upon the completion of step 228, a complete list has been obtained of physicians, health care providers and advertisements to be included in the directory. In addition, an appropriate number of advertisements and discount coupons have also been selected for inclusion in the directory. All of the selected physicians and health care providers, advertisements and coupons are for physicians, providers and businesses having offices within the geographic region corresponding to the customer. The only exception may be for physicians and health care providers that the customer has previously used for treatment. An adaptation of the determination of the geographic region is to include in the geographic region surrounding the customer the area nearby those physicians and providers that the customer has previously used for treatment. Similarly, the geographic region corresponding to the customer may be selected to include the office address of the customer's employer. Accordingly, the geographic region corresponding to the customer need not be only that region surrounding the customer's residence address, but may be other geographic regions, such as that surrounding the customer's employer, that the customer is known to regularly visit based on information in the customer database 110.

In step 230, a street map for the geographic region surrounding or otherwise corresponding to the customer is generated by the computer processor 104. The map is stored in memory location 122. Once the street map is generated, the addresses for the customer and the selected physicians, health care providers and advertisers are plotted on the map in step 232. The plotted street map is stored in map directory 122, and the other information, customer name and address, physicians' names and addresses, etc., are stored in the corresponding memory locations 116, 118 and 120. The map and other data are stored in memory and await commands from the computer processor and/or variable print engine 102 for merging with the template directory stored in location 124 in step 234.

When the computer processor 104 issues a print command for the variable print engine, the processor and/or variable print engine access the template directory from memory location 124 and in printing the template directory use the field codes in the template directory to obtain the variable information from those memory locations having the variable information. For example, the template directory may have a map field code that points the variable print engine to the memory storage area 122 for the map to be included in the directory being printed. Similarly, field codes in the template directory for the memory location for the customer name, physicians to be listed, images and advertising and coupons are used by the variable print engine and/or computer processor to obtain variable information from each of those memory locations. The template directory and the variable print information identified by the fields codes in the template directory are merged together to generate a complete template directory that is printed by the variable print engine 102 to form a printed high-quality directory 116 that may include color photographs and other high-quality printing features. After the directories are printed in step 236, the process repeats itself in step 238 for the next customer for whom a directory is to be printed.

Figure 3A:
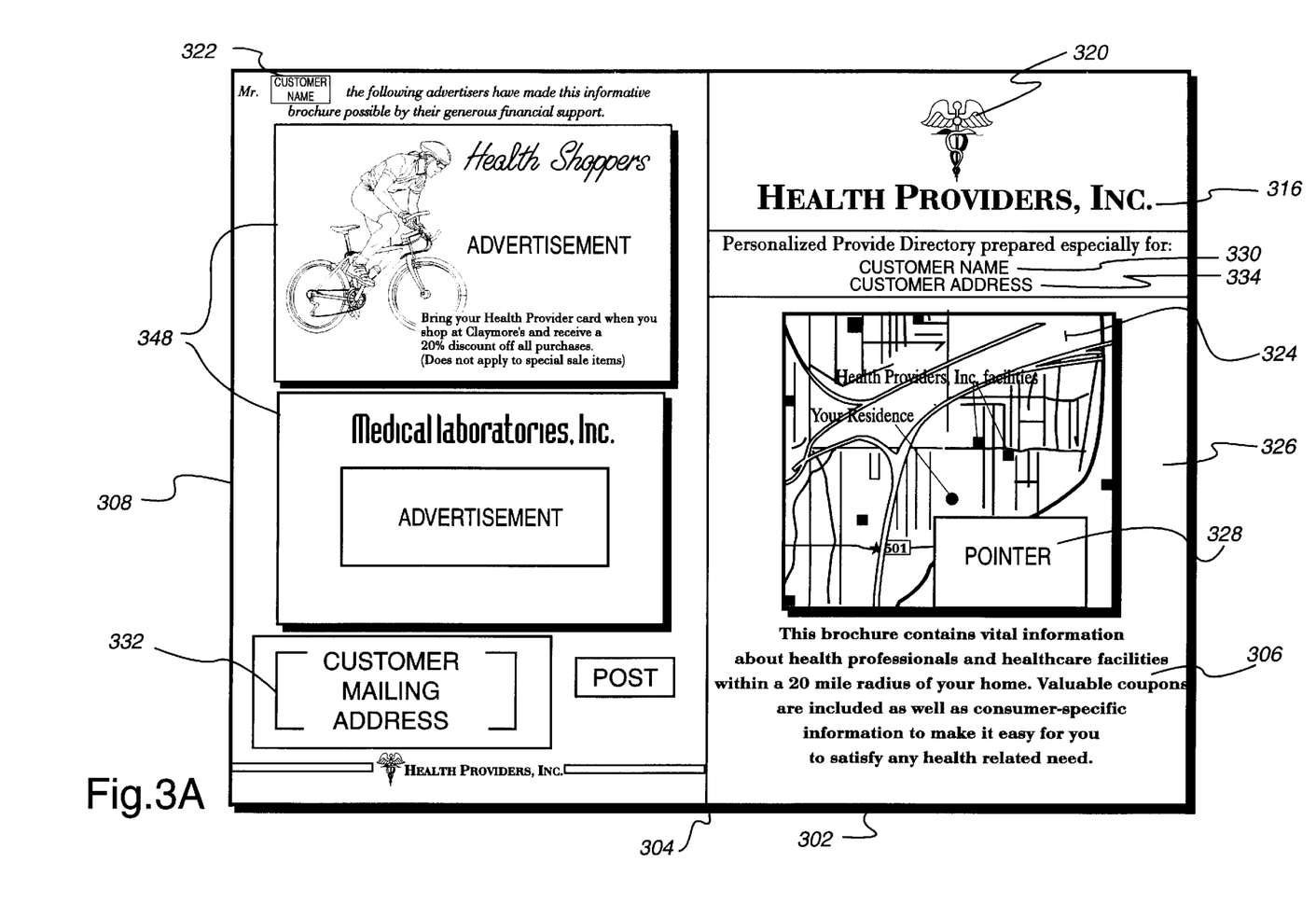
Figure 3B:
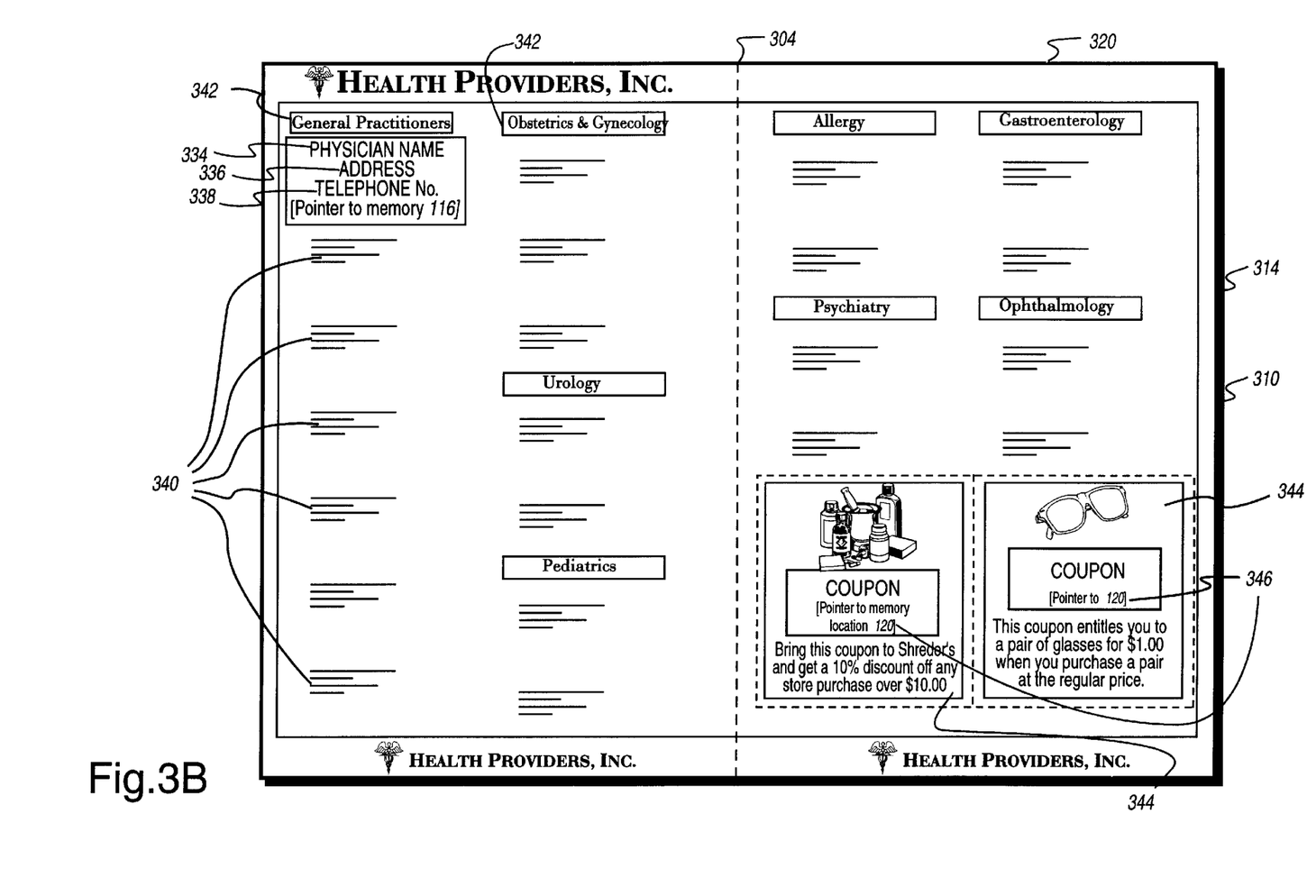

FIGS. 3A and 3B show a front and back view, respectively, of an exemplary personalized health care directory 302. The directory is a single sheet folded along a fold line 304 to form a four-page directory having a front page 306, a back page 308 and a left and right center page 310 and 312, respectively.

The first page 306 of the brochure may include fixed text identifying the health care service provider 316 and fixed text describing the brochure. Fixed text is text that is to be printed on each and every health care directory and may be included in the template directory for the brochure. In addition to fixed text, fixed logos and images may be included in the template directory such as the medical logo 320 shown on the first page 306 of the directory. In addition, fixed text and/or images may be placed on other pages of the printed document. Furthermore, fixed text information and images may be combined with variable information. For example, a fixed text message may include a blank field 322 for insertion of a customer name from the memory location 118. The customer name data field 322 may include a hidden command code that directs the computer processor or variable print engine to read the customer name from the appropriate database field in the memory location 118.

A map 324 may be presented on the front page 306 of the brochure 302. The map 324 is obtained from the map memory location 122 associated with the computer processor. The map is inserted in a blank field 326 that defines a region of the brochure 302 into which the map is to be inserted. The blanked-out block field 326 for the map that is included in the directory template may include a command 328 pointing the computer processor or variable print engine to the map memory location 122. Similarly, variable print information fields may be located on the front page of the brochure 302 for the customer name 330 and the customer address 332. The variable print fields for the customer name and customer address may define a region of the front page of the brochures, e.g., by specifying a number of available characters, for both the customer name and address. In addition, the customer name and customer address fields on the template directory may include embedded pointer commands that direct the variable print engine or computer processor to read the customer name and customer address from the memory storage locations 118.

The second page 312 and third page 314 of the brochure may include variable fields for listing physician and other health care providers. For each physician, there may be an associated variable field for the physician's name 334, a field for the physician's address 336 and the physician's telephone number 338. Each of these data fields, 334, 336, 338 may include embedded pointers to particular memory locations in the memory for the physicians 116. Additional variable data fields for physicians 340 may be laid out in the brochure 302.

Physicians and other health care providers to be listed in the directory can be arranged by specialties. A variable data field for specialties 342 may be placed on the directory template as a heading. The variable data field for the specialty may include an embedded pointer to a memory location in the memory location 116 for physician and health care provider selected for the directory to be printed. Below each specialty heading can be inserted the data fields for the physician's name, address and telephone number.

In the template directory a variable data field can be inserted for advertising coupons 344, the coupon data field may be blocked out to allow for printing of a coupon having both image and text. The coupon data field may include a pointer 346 to a memory location for images 120. The coupon data field is generally located such that it may be cut out without deleting any of the listed physicians from the directory. In addition, advertisements may be imprinted in the directory through the use of variable data fields 348 for advertisements. As with coupons, the advertisements may be blocked out to receive variable images and text corresponding to the advertisement. The advertisement fields may included embedded codes pointing to a memory location in the image memory location 120 for the corresponding advertisement.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for printing a group physician directory using a computer system having access to databases for customers of a health care provider service, for group physicians that are members of the health care provider service, for advertisers and corresponding advertisements, and for mapping data, and a printer, where the method comprises the following steps:

a. designing a directory template having fields for a customer name, customer address, a listing of group physician names and addresses, an advertisement, and a map;

b. selecting a customer name from a listing of customers for which personalized health care provider directories are to be printed;

c. for a customer selected in step (b), obtaining from the customer database information regarding an address for the customer;

d. determining a geographic region corresponding to the address of the customer;

e. accessing the database for group physicians, and selecting group physicians having office addresses within the geographic region determined in step (d);

f. if the physicians selected in step (e) exceeds a threshold number of physicians, then restricting the physicians selected to the threshold number;

g. accessing the database for advertisers and advertisements to select advertisers having office addresses near the customer and selecting advertisements corresponding to the selected advertisers,     h. generating a map of the geographic region determined in step (d) and plotting on the map the addresses of the customers, the physicians selected in steps (e) and (f), and the advertisers selected in step (g);

i. importing information into the respective fields of the template of the health care provider directory, the information including the customer name selected in step (b), the customer address obtained in step (c), the group physicians selected in steps (e) and (f), the advertisements selected in step (g), and the map generated in step (h); and     j. printing the directory by printing the template of the health care directory with the information imported into the template in step (i).

2. A method for printing a group physician directory as in claim 1 step (g) is further performed by selecting an advertisement for the selected advertiser, wherein the advertiser is selected to be a health care business located within the geographic region defined in step (d) and which health care business corresponds to a medical specialty of one or more of the physicians selected in steps (e) and (f).

3. A method for printing a group physician directory as in claim 1 wherein the group physicians selected in step (e) include health care providers other than physicians.

4. A method of printing a group physician directory as in claim 1 wherein step (d) is repeated to expand the geographic region corresponding to the address of a customer, if a number of group physicians selected in step (e) is below a predetermined threshold number of group physicians.

5. A method of printing a group physician directory as in claim 1 wherein step (e) further includes identifying group physicians that have previously treated the customer by accessing the customer database to identify the group physicians that have treated the customer.

6. A method of printing a group physician directory as in claim 1 wherein step (e) further includes sorting the selected group physicians by their specialties.

7. A method of printing a group physician directory as in claim 1 wherein step (e) further includes choosing at least one physician specialty, and limiting the selected physicians to those having the chosen specialty.

8. A method of printing a group physician directory as in claim 7 wherein step (e) further includes choosing the at least one physician specialty by correlating data obtained about the customer from the customer database with a listing of specialties for physicians.

9. A method of printing a group physician directory as in claim 1 wherein step (f) further comprises plotting on the map the office addresses of the group physicians selected in step (e).

10. A personalized group physician health care directory comprising:

a customer name and address printed on the directory where the customer is selected from a customer database;

a listing of group physicians having office addresses in a geographic area corresponding to the address of the customer, wherein at least one of the group physicians included in the listing has a medical specialty that identified in the listing;

one or more coupons advertising health care businesses providing products corresponding to the medical specialty of the at least one of the group physicians included in the listing, and     a map of the geographic area, where the addresses of the listed group physicians are plotted on the map.

11. A personalized group physician health care directory as in claim 10 further comprising a listing of group physicians who have previously treated the customer.

12. A personalized group physician directory as in claim 10 wherein the health care businesses having office addresses plotted on the map.

13. A personalized group physician directory as in claim 10 printed on a single sheet.

14. A personalized group physician directory as in claim 10 wherein the listing of group physicians is arranged by physician specialties, and the specialties are selected specifically for the customer.

15. A personalized group physician directory as in claim 10 wherein the listing of group physicians further includes health care providers other than physicians.

\* \* \* \* \*